United States Patent [19]
Arndt et al.

[11] Patent Number: 5,904,648
[45] Date of Patent: *May 18, 1999

[54] GUIDED ENDOBRONCHIAL BLOCKER CATHETER

[75] Inventors: George A. Arndt, Madison, Wis.; Frank J. Fischer, Jr., Bloomington, Ind.

[73] Assignee: Cook Incorporated, Bloomington, Ind.

[21] Appl. No.: 08/878,448

[22] Filed: Jun. 18, 1997

Related U.S. Application Data

[60] Provisional application No. 60/020,452, Jun. 18, 1996.

[51] Int. Cl.$^6$ .......................................... A61B 1/22
[52] U.S. Cl. ......................... 600/120; 600/114; 600/110; 606/108
[58] Field of Search ..................................... 606/108, 110, 606/113, 114; 604/101–103, 193–196, 96–104; 600/120, 114, 194, 101; 128/207.15, 207.14, 911

[56] References Cited

U.S. PATENT DOCUMENTS

| | | |
|---|---|---|
| 3,435,826 | 4/1969 | Fogarty . |
| 3,448,739 | 6/1969 | Stark et al. . |
| 3,734,100 | 5/1973 | Walker et al. . |
| 3,833,003 | 9/1974 | Taricco . |
| 3,880,168 | 4/1975 | Berman . |
| 4,248,221 | 2/1981 | Winnard . |
| 4,453,545 | 6/1984 | Inoue . |
| 4,762,125 | 8/1988 | Leiman et al. . |
| 4,819,664 | 4/1989 | Nazari . |
| 4,886,496 | 12/1989 | Conoscenti et al. . |
| 4,976,261 | 12/1990 | Gluck et al. . |
| 4,988,356 | 1/1991 | Crittenden et al. ...................... 606/192 |
| 5,103,804 | 4/1992 | Abele et al. . |
| 5,136,942 | 8/1992 | Rydell ..................................... 606/110 |
| 5,315,992 | 5/1994 | Dalton . |
| 5,417,684 | 5/1995 | Jackson et al. .......................... 606/113 |
| 5,607,386 | 3/1997 | Flam . |
| 5,730,702 | 3/1998 | Tanaka et al. ........................... 600/180 |

OTHER PUBLICATIONS

Muschin W.W., *Thoracic Anaesthesia*, Oxford England: Blackwell Scientific Publications, 1963, pp. 270,272.

Package insert for the Univent Tube, Fuji Systems Corporation, Tokyo, Japan.

Ginsberg R.J., "New technique for one–lung anesthesia using an endobronchial blocker," *J. Thorac Cardiovasc Surg* 82:542–546, 1981.

Kaplan J.A., *Thoracic Anesthesia*, New York: Churchill Livingstone, 1983, pp. 389–402.

Larsen et al., "A Device for Endobronchial Blocker Placement During One–Lung Anesthesia", ANESTH ANALG 1990; 71:311,312.

Westhorpe R., "Magill's Endobronchial Tubes", *Anaesthesia and Intensive Care*, vol. 20, No. 4, Nov., 1992, p. 409.

Arndt et al., "Co–axial placement of endobronchial blocker," *Canadian Journal of Anaesthesia*, pp. 1126, 1127.

*Primary Examiner*—Gary Jackson
*Assistant Examiner*—Lien Ngo
*Attorney, Agent, or Firm*—Richard J. Godlewski

[57] ABSTRACT

A balloon-tipped, wire-guided double lumen, endobronchial blocker catheter (6) is provided for insertion into the tracheal bronchial tree using a fiberoptic bronchoscope (2). The catheter incorporates a removable wire guide (14), which runs the entire length of the catheter exiting the tip as a small unencased wire loop (12). The small unencased wire loop is positioned around the circumference of a fiberoptic bronchoscope and when advanced along the fiberoptic bronchoscope thereby allows the catheter to navigate the airway using the fiberoptic bronchoscope as a guide or stint allowing the catheter to reach portions of the lung where access is difficult due to sharp bends in the tracheal bronchial tree. A balloon (8) thereof is inflated to provide obstruction of a portion of the lung from ventilation. The long wire guide loop is removable allowing communication of the blocked segment with the proximal end of the catheter.

20 Claims, 5 Drawing Sheets

FIG. 9

GUIDED ENDOBRONCHIAL BLOCKER CATHETER

CROSS-REFERENCE TO RELATED COPENDING APPLICATIONS

This application claims priority of provisional application Ser. No. 60/020,452, filed Jun. 18, 1996. This application also claims priority to Disclosure Document No. 391191, received by the USPTO on Jan. 30, 1996 and Disclosure Document No. 356006, received by the USPTO on Jun. 14, 1994.

TECHNICAL FIELD

The present invention relates generally to medical devices and, particularly, to a balloon catheter for obstructing ventilation to a portion of the lung.

BACKGROUND OF THE INVENTION

Patients who are critically ill or undergoing surgical procedures involving the lungs (thoracic surgery) frequently require a portion of the lung to be isolated from mechanical ventilation. The lungs are located in the chest cavity and bounded by the chest wall and the diaphragm, a thin muscular membrane. The lungs are held next to the chest wall by negative pressure and a thin fluid layer. The space of opposition is the pleural space. The lungs are made of the trachea, an air conduit, and the lung tissue which abuts against the chest wall. The trachea divides in the chest cavity into two separate air conduits, a right sided air conduit (the right mainstem bronchus) and a left sided air conduit (the left mainstem bronchus). The left mainstem bronchus makes a greater angle than the right mainstem bronchus, and the passage of catheters into the left mainstem bronchus is difficult.

Ventilation is a physiologic process which supplies oxygen to the body and removes carbon dioxide, a gaseous waste product. Ventilation is provided by the rhythmic back and forth motion of air in the trachea. Air enters and exits through the mouth connected to the trachea. In health, the rhythmic motion of air is provided by the rhythmic contraction and relaxation of the diaphragm. In surgical patients and the critically ill, ventilation is commonly provided mechanically using a mechanical ventilator and an endotracheal tube. An endotracheal tube is a balloon tipped catheter open at both ends, which is positioned in the mid trachea. It is connected to the mechanical ventilator to provide ventilation.

Isolation of ventilation is required commonly. In thoracic surgery, the chest wall is incised, the lung opened and the pleural space entered. As a result, the lung will collapse, and ventilation can escape. The ventilation to the nonoperative lung must be isolated before opening the operative lung segment. The risk of patient harm exists if ventilation is not isolated before beginning thoracic surgery. This results from the escape of ventilation through the surgical lung opening. Isolation of ventilation is commonly required in medical patients. A portion of the lung can be diseased and requires isolation from mechanical ventilation. Conditions which require isolation are infection of the lung (pneumonia); bleeding in the lungs (hemoptysis); and a non-surgical opening into the pleural space (pneumothorax).

A double lumen endotracheal tube is a commercially available device to achieve isolation of ventilation. A double lumen endotracheal tube is made of two endotracheal tubes fused together of unequal length. It incorporates two balloons, one balloon which envelopes the tracheal position of the two fused endotracheal tubes (the tracheal balloon) and a second which envelopes the longer portion and will extend into either the right or left mainstem bronchus (the bronchial balloon). A double lumen tube will isolate ventilation when positioned correctly with the longer portion in the right or left mainstem bronchus, and both balloons are inflated. There are disadvantages in using double lumen endotracheal tubes. Double lumen endotracheal tubes are larger in diameter and longer than conventional endotracheal tubes and can damage the vocal chords and the nerves for the vocal chords. The left mainstem bronchus is difficult to enter with the longer portion. In patients where the normal airway anatomy is altered, the use of double lumen endotracheal tubes has caused patient harm. Due to the complexity and size, hypoxic brain damage has occurred because of the time needed to correctly place the device in the airway. A double lumen endotracheal tube can not be left in place for long periods of time. Due to its size, it can cause damage of the tracheal bronchial tree including disruption.

An endobronchial blocker is another device to achieve isolation of ventilation. An endobronchial blocker is a balloon tipped catheter, which is placed using a fiberoptic bronchoscope. The balloon is positioned in either the right or left mainstem bronchus. The balloon is inflated to achieve isolation of ventilation. A commercially available vascular, balloon-tipped catheter is used routinely for an endobronchial blocker to achieve endobronchial blockade. The vascular, balloon-tipped catheter has disadvantages. The vascular, balloon-tipped catheter is not coupled to the motion of the fiberoptic bronchoscope. The fiberoptic bronchoscope is used only to view the vascular, balloon-tipped catheter when positioning the catheter. The operation of the fiberoptic bronchoscope and vascular, balloon-tipped catheter are entirely independent. The vascular, balloon-tipped catheter is very difficult to place in the left mainstem bronchus. It routinely requires several attempts to position correctly. The vascular, balloon-tipped catheter uses a removable stiff mandrel wire, placed in the catheter lumen, to allow manipulation during placement. This can cause tissue trauma due to the stiffness of the end portion. The vascular, balloon-tipped catheter incorporates only a single lumen in the design. This lumen accepts the removable mandrel wire and allows inflation of the balloon with the mandrel wire removed. The single lumen does not allow gas to be aspirated from the blocked section, gas to be added to the blocked section, irrigation fluid to be added to the blocked section, and irrigation fluid, secretions or blood to be removed from the blocked section. The balloon of the vascular, balloon-tipped catheter is not optimal. The inflated balloon is spherical in shape allowing easy dislodgement. The balloon is of a low volume, low compliance, high pressure, spherical type designed to be filled with fluid to remove blood clots from blood vessels. This type of balloon can transmit excessive pressure to the tracheal wall causing damage. The balloon has no mechanism to sense the inflation pressure.

A Univent tube is another commercially available device to achieve isolation of ventilation. A Univent tube is an endotracheal tube designed with a large lumen and a small lumen. The large lumen allows ventilation using conventional means. The smaller lumen accepts an endobronchial blocker. The endobronchial blocker is advanced into the right or left mainstem bronchus, and the balloon is inflated to achieve isolation of ventilation. The remaining portion of the Univent tube remains in the trachea in the same fashion as a conventional endotracheal tube.

The Univent tube has disadvantages. The endobronchial blocker can be difficult to place in the left mainstem bronchus. It should be placed using a fiberoptic bronchoscope. The motion of the fiberoptic bronchoscope and the blocker are entirely independent. In clinical practice, the Univent tube is larger in diameter than a conventional endotracheal tube. This can lead to difficulty in placement and damage to the vocal chord mechanism. The ventilation lumen of the Univent tube is smaller in cross-sectional than that of a similar sized conventional endotracheal tube. In patients with severe pulmonary disease, this smaller cross-sectional area can make removal of the Univent tube at the conclusion of surgery difficult. The work of breathing through this small lumen is higher and there is the risk of ventilatory failure.

SUMMARY OF THE INVENTION

The foregoing problems are solved and a technical advance is achieved in an illustrative balloon tipped catheter and method for blocking an anatomical passage of a patient. When preferably utilized in the tracheo-bronchial tree of a patient, the catheter and method are utilized to achieve endobronchial blockade. The catheter comprises an elongated tubular member with first and second lumens therein and an inflatable, blocker balloon disposed about a distal portion of the elongated tubular member. The first lumen is for balloon inflation, and the second larger lumen is for encasing a removable filament or wire guide. The wire guide extends as a large loop from the proximal end of the elongated member to the distal end thereof, where the loop extends distally as a small unencased wire guide loop. The wire guide loop can be removed after correct positioning. This advantageously allows gas or fluid to be removed or added to the blocked segment through the large lumen.

An advantage of the present invention is the small unencased wire guide loop, which is guided by a fiberoptic bronchoscope to greatly facilitate placement and positioning of the endobronchial blocker catheter.

A fiberoptic bronchoscope is a flexible triple lumen tube. Two lumens contain an optical viewing fiber, and an optical lighting fiber. The third lumen is a channel for suction. The fiberoptic bronchoscope incorporates a tip control mechanism to allow the visualization and navigation of the tracheo-bronchial tree. The bronchoscope is commonly used to inspect the tracheo-bronchial tree and, using the controlled tip, inspect portions of the bronchus with sharp bends such as the left mainstem bronchus.

To more easily allow placement of an endobronchial blocker catheter, the fiberoptic bronchoscope is guided through the small unencased wire guide loop after the endobronchial blocker catheter has been advanced into a conventional endotracheal tube. The fiberoptic bronchoscope is advanced down the tracheo-bronchial tree until the portion of the lung to be isolated from ventilation is reached. The endobronchial blocker catheter is then advanced along and guided by the fiberoptic bronchoscope until the small unencased wire guide loop exits off the tip of the bronchoscope. The tip of the endobronchial blocker catheter is in view after the unencased wire guide loop exits the tip of the bronchoscope. The fiberoptic bronchoscope acts as a guide for the endobronchial blocker and is capable of navigating sharp turns such as the left mainstem bronchus, which an unguided blocker is incapable of. This wire guided catheter and method allows the endobronchial blocker catheter to be placed quickly and atraumatically as compared to the prior art. The aforementioned technique is used to guide any catheter into the airway using a fiberoptic bronchoscope to allow accurate and timely placement.

Another advantage of the present invention is the design of the balloon. The balloon is elliptical in shape when inflated to allow maximum contact area between the balloon and bronchial wall. The elliptical shape minimizes the chance of dislodgement by surgical manipulation of the lung. A spherical balloon shape, as in the prior art, is not optimal as the contact area is minimized to the circumference of the balloon and the bronchial wall. The balloon incorporates at the proximal end a spring loaded valve with a pneumatic bladder. This allows tactile sensation of the balloon inflation pressure. The balloon is of the high compliance, high volume, low pressure type. It inflates with a minimum of pressure to minimize bronchial damage. The balloon is optimally inflated with air.

Still another advantage of the present invention is the physical characteristics of the catheter. The distal portion of the catheter including the balloon is designed to be soft and pliable to minimize damage during advancement and positioning. The remaining portion of the catheter is not deformable and less pliable incorporating several mandrel wires into the plastic matrix material of the catheter during the manufacture process. The mandrel wires allow a high degree of rotational torque at the proximal end that is transmitted to the distal end to aid in catheter advancement and positioning. The catheter also utilizes radiopaque material to allow visualization using a roentgenogram or fluoroscopy.

Yet another advantage of the present invention is the ability to use a conventional endotracheal tube for endobronchial blocker catheter placement. The use of a conventional endotracheal tube allows the cross sectional area of the endotracheal tube to be maximized while minimizing the external diameter and size.

At least one end of the loop of the blocker catheter is also fixed relative to the proximal end of the catheter. Additionally, both ends can be affixed using, for example, a set screw in an end cap threadably engaged with the proximal end of the catheter. This advantageously allows the wire guide as well as the unencased loop extending distally from the catheter to be aligned for placement around the fiberoptic bronchoscope. Furthermore, the threaded end cap advantageously permits sizing of the loop around the bronchoscope. Should additional sizing or tension of the loop be desired, one end of the loop extends past the proximal end of the catheter and can be pulled to decrease the size of the loop or pushed to increase its size. A clamp such as a cam lock and cam support fixture is disposed about the proximal end of the catheter for releasably engaging the free end of the wire guide loop.

The blocker catheter can also advantageously include a guide extending from the distal end of the catheter for engagement with an endoscope for guiding the blocker balloon into an airway passage. This advantageously eliminates the need for a second lumen in the catheter should it not be desired. The guide includes a loop for circumferentially surrounding a bronchoscope positioned therethrough and for guiding the catheter to the desired position in the tracheo-bronchial tree.

DETAILED DESCRIPTION

Figure 1:
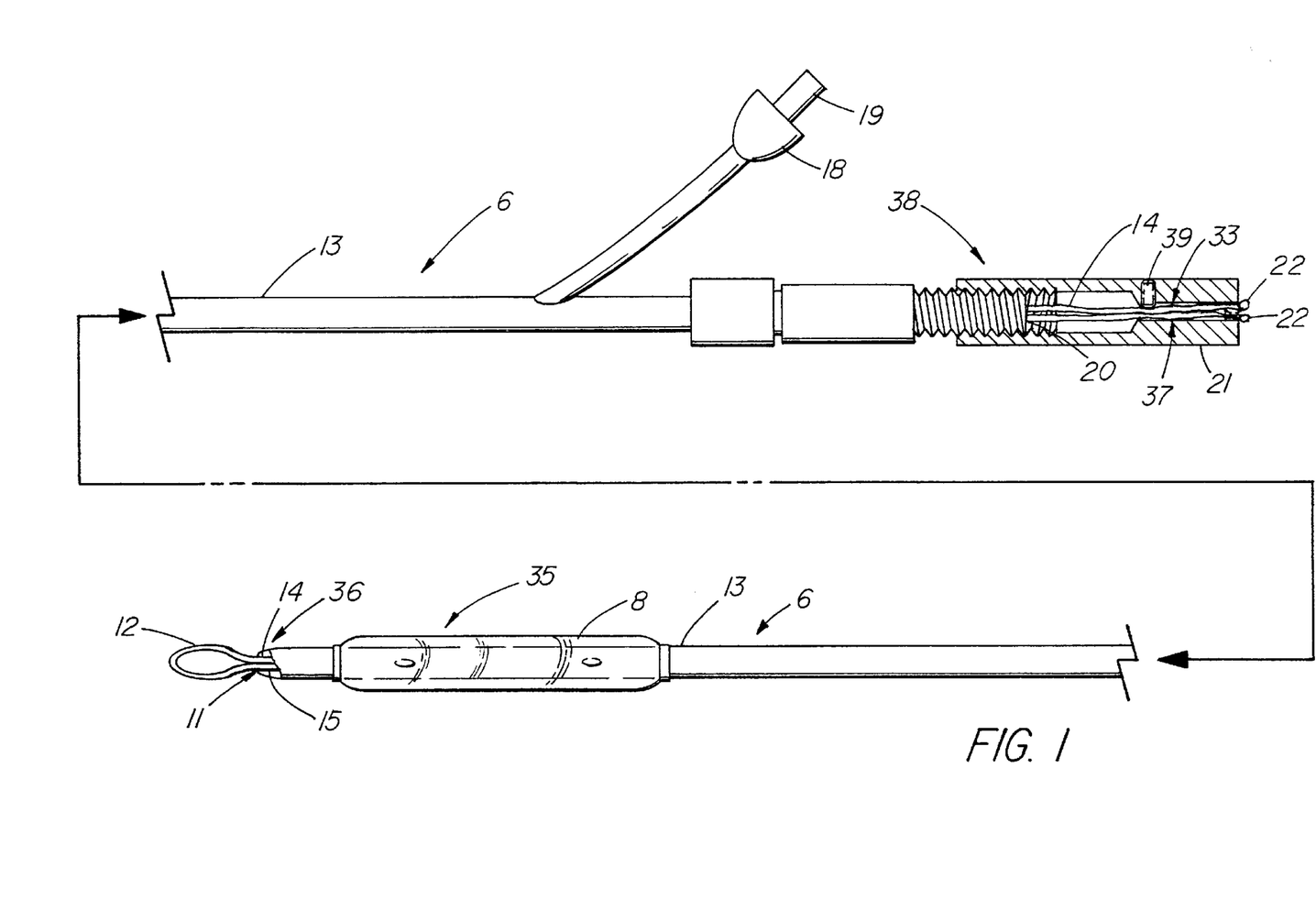
FIG. 1 depicts a partially sectioned side view of a preferred illustrative embodiment of an endobronchial blocker catheter of the present invention.

FIG. 1 depicts a partially sectioned side view of a preferred illustrative embodiment of endobronchial blocker catheter 6 of the present invention including an elongated member such as tube 13 with a filament or wire guide 14 encased in large lumen 15 of the elongated member or tube. Loop 12 of the wire guide extends distally from the encased portion of the wire guide and end hole 11 of large lumen 15. Proximal ends 37 of the looped or folded back wire guide are affixed to proximal end 38 of the catheter via attachment points 22 and a clamp such as set screw 39. An inflatable blocker balloon 8 is disposed about distal portion 35 of the elongated member or tube.

Figures 2, 3, 4:
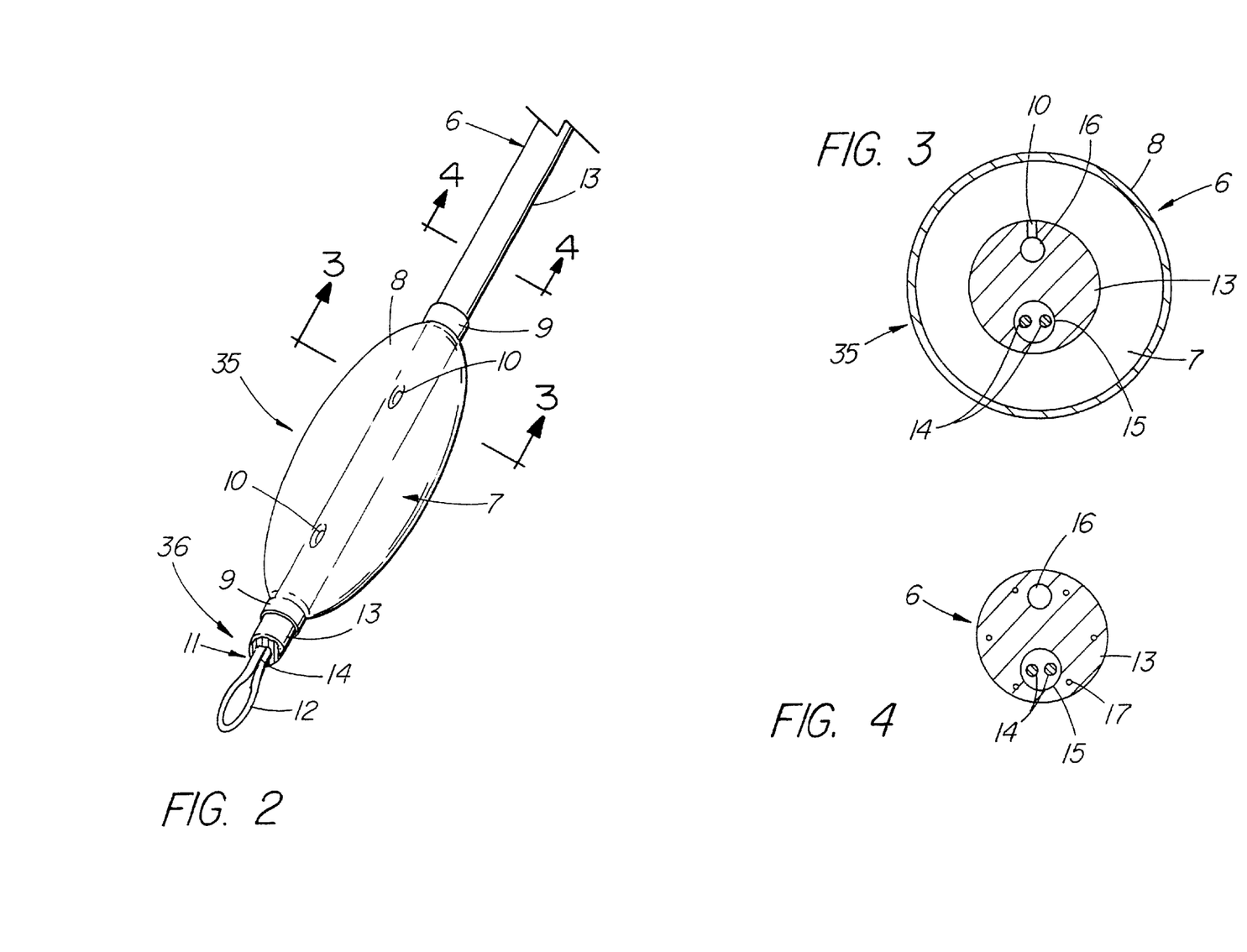
FIG. 2 depicts an enlarged, partially sectioned pictorial view of he distal portion of the endobronchial blocker catheter of FIG. 1 with the balloon thereof in an inflated state.
FIG. 3 depicts an enlarged cross-sectional view of the endobronchial blocker catheter of FIG. 2 taken along the line 3—3.
FIG. 4 depicts an enlarged cross-sectional view of the endobronchial blocker catheter of FIG. 2 taken along the line 4—4.

FIG. 2 depicts an enlarged, partially sectioned pictorial view of distal portion 35 of endobronchial blocker catheter 6 of FIG. 1 with blocker balloon 8 in an inflated state. Balloon 8 is made from a conventional elastomeric material such a latex, polyurethane, silicone rubber or silicone plastic. The leading and trailing ends of balloon 8 are attached to elongated member or tube 13 at balloon attachment points 9 using a conventional non-brittle, medical grade adhesive. The balloon forms an elliptical shape when interior 7 of the balloon is inflated via one or more exit ports 10 that communicate with an inflation lumen in the tube.

FIG. 3 depicts an enlarged cross-sectional view of the distal portion of endobronchial blocker catheter 6 of FIG. 2 taken along line 3—3 with balloon 8 inflated. The catheter comprises an elongated tubular member 13 formed from a conventional pliable radiopaque plastic such as polyurethane, fluroplastic, polyester, nylon, polypropylene or silicone plastic. Tubular member 13 includes wire guide lumen 15 and balloon inflation lumen 16. The small balloon inflation lumen 16 is closed at the distal end thereof by heating the distal end of the elongated member above its melting point causing small balloon inflation lumen 16 to communicate only with interior 7 of balloon 8 via port 10. Large wire guide lumen 15 contains and encases folded back wire guide 14 with loop 12 extending from the distal end thereof.

FIG. 4 depicts a cross sectional view of the endobronchial blocker catheter of FIG. 2 taken along the line 4—4 above or proximal balloon attachment point 9 and above or proximal exit port 10 of balloon inflation lumen 16. Balloon inflation lumen 16 is present and is continuous with a proximal pneumatic inflation bladder 18 with a connecting tubing and self sealing spring valve 19 as depicted in FIG. 1. Elongated member 13 also includes a plurality of mandrel wires 17 extending longitudinally therein. The mandrel wires are incorporated into plastic elongated member or tube 13 during the process of die extrusion and do not extend through distal portion 35. Folded back wire guide 14 in lumen 15 extends through the catheter member 13 to the proximal end thereof. When the encased wire guide 14 has been removed, large lumen 15 of the endobronchial blocker catheter is in communication from the threaded proximal end port 20 to end hole 11 and the sealed lung segment when the balloon is inflated.

The encased wire guide 14 attaches to threaded, proximal end cap 21 at attachment points 22 as depicted in FIG. 1. The encased wire guide 14 is affixed to the blocker catheter via the threaded port 20 by screwing the threaded end cap 21 to the threaded port 20. The encased wire guide 14 and unencased wire guide loop 12 can be removed from endobronchial blocker catheter 6 by unscrewing end cap 21 from threaded port 20 and pulling the encased wire guide 14 out of the endobronchial blocker catheter. With the encased wire guide 14 removed, communication between the sealed lung segment and proximal end 38 of the endobronchial blocker catheter is provided by large lumen 15. Balloon inflation lumen 16 controls the inflation and deflation of blocker balloon 8. The proximal end of the balloon inflation lumen is attached in a well-known manner to a pneumatic inflation bladder 18 with connection tubing. The pneumatic inflation bladder at the proximal end includes a self sealing spring valve 19, which allows the inflation and deflation of balloon 8 through the balloon inflation lumen 16 using a gas or fluid. The threaded end cap 21 can be advanced or retracted with respect to proximal end 38 of elongated member or tube 13. Pushing or pulling the encased wire guide 14 increases or decreases the size of the unencased wire guide loop 12. In addition, the end cap along with proximal ends 37 of the wire guide are rotatable relative to elongated member 17 to rotate loop 12 and provide alignment with an endoscope that is being positioned or guided through the loop.

Figure 5:
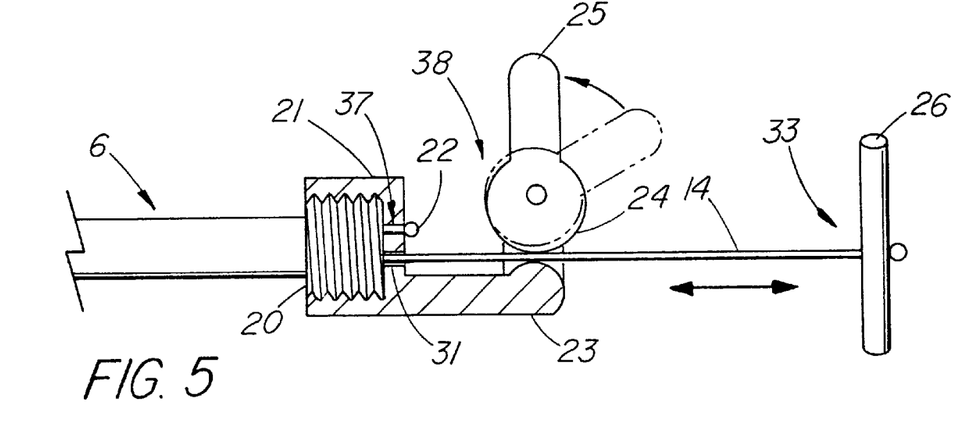
FIG. 5 depicts a partially sectioned view of another embodiment of the end cap of the endobronchial blocker catheter of FIG. 1.

FIG. 5 depicts a partially sectioned side view of an alternative embodiment of end cap 21 of endobronchial blocker catheter 6 of FIG. 1. This embodiment can also alter the size of unencased wire guide loop 12. Free end 33 of encased wire guide 14 travels through wire guide hole 31 of threaded end cap 21 and between locking cam 24 and cam support arm 23 and attaches to tensioner handle 26. Tensioner handle 26 is pulled or pushed to retract or advance free end 33 of wire guide 14 through end cap hole 31, thereby changing the size of unencased wire guide loop 12. The other end 37 of the wire guide is affixed at attachment point 22. A clamp such as cam lever 25 is advanced or retracted to lock or unlock free end 33 of encased wire guide 14 or unencased loop 12 between cam 24 and cam support arm 23.

Figure 6:
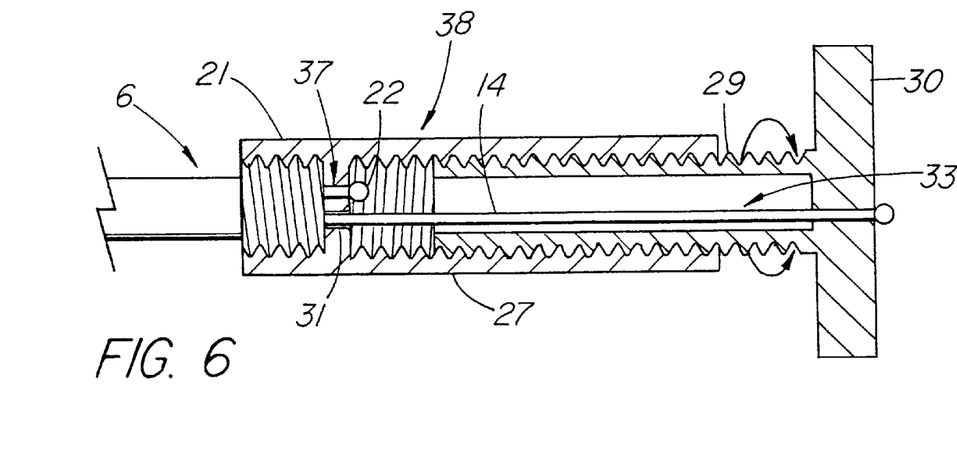
FIG. 6 depicts a partially sectioned view of yet another embodiment of the end cap of the endobronchial blocker catheter of FIG. 1.

FIG. 6 is a partially sectioned view of another alternative embodiment of end cap 21 to alter the size and/or the tension of the unencased wire guide loop 12 of endobronchial blocker catheter 6 of FIG. 1. The free end 33 of wire guide 14 travels through end cap wire guide hole 31, internally threaded fitting 27 affixed to threaded end cap 21, and through hollow screw 29, and knob 30 that is affixed to the hollow screw. A clamp such as threaded hollow screw 29 is threaded in or out of internally threaded plastic fitting 27 by turning the threaded hollow screw knob 30, thereby increasing or decreasing the size and/or the tension of wire guide wire loop 12.

Figure 7:
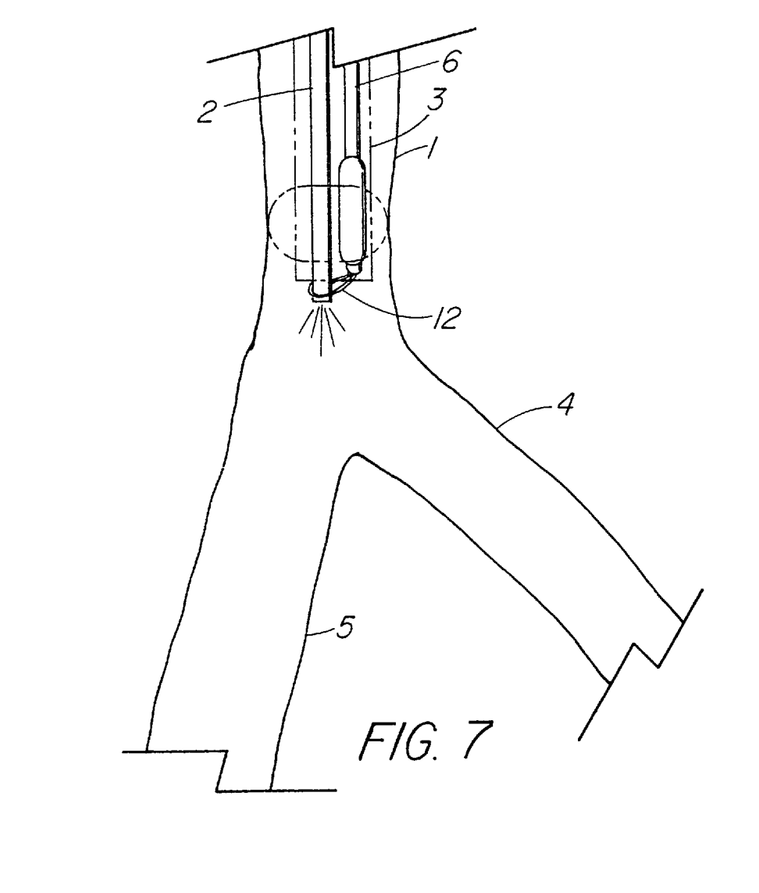
FIG. 7 depicts a profile view of a trachea with a fiberoptic bronchoscope passing through the unencased wire guide loop snare of the endobronchial blocker catheter of FIG. 1.

FIGS. 7–10 depict a preferred method of using the fiberoptically directable wire guided endobronchial blocker catheter 6 of FIG. 1. FIG. 7 depicts a fiberoptic bronchoscope 2 and endobronchial blocker catheter 6 with wire guide loop 12 extending distally therefrom that are inserted through endotracheal tube 3 with an inflated balloon, previously inserted into trachea 1. The fiberoptic bronchoscope 2 is advanced through the unencased wire guide loop 12 using the optics of the fiberoptic bronchoscope or using direct visualization through the clear plastic endotracheal tube. The bronchoscope incorporates a well-known, articulated tip control mechanism that permits continued visualization and navigation. Once the fiberoptic bronchoscope 2 is advanced through unencased wire guide loop 12, the fiberoptic bronchoscope is advanced to the desired location in the tracheo-bronchial tree.

Figure 8:
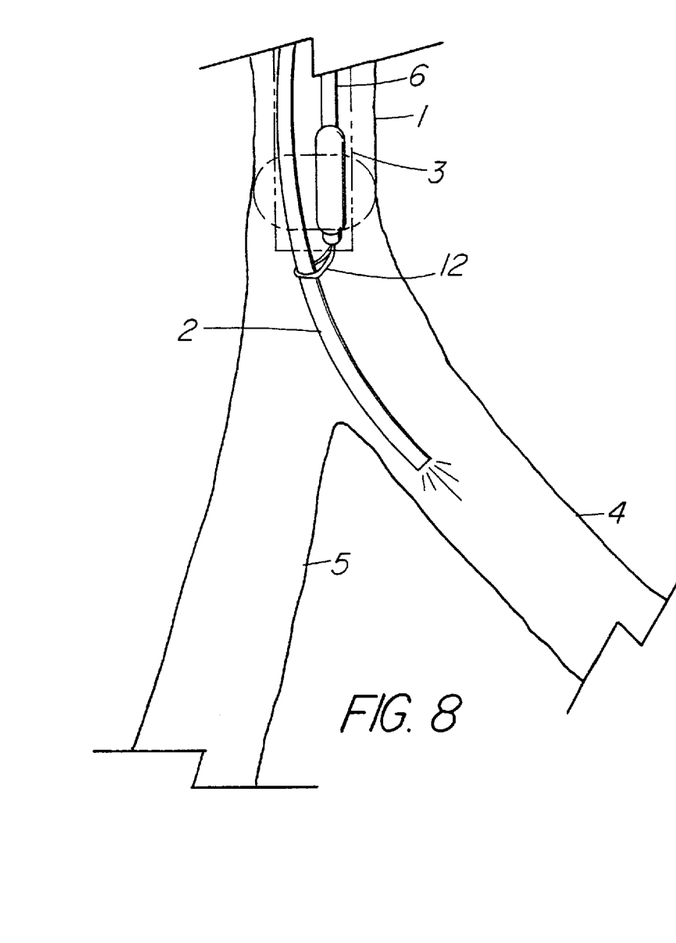
FIG. 8 depicts a profile view of the trachea with the fiberoptic scope advanced into the left mainstem bronchus of a patient.

The fiberoptic bronchoscope 2 is able to make sharp turns and navigate the tracheo-bronchial tree using the optics of the fiberoptic bronchoscope 2. In FIG. 8, the fiberoptic bronchoscope 2 has entered left mainstem bronchus 4, which in practice, is difficult to enter with a catheter, because of the sharp angle it makes with trachea 1.

Figure 9:
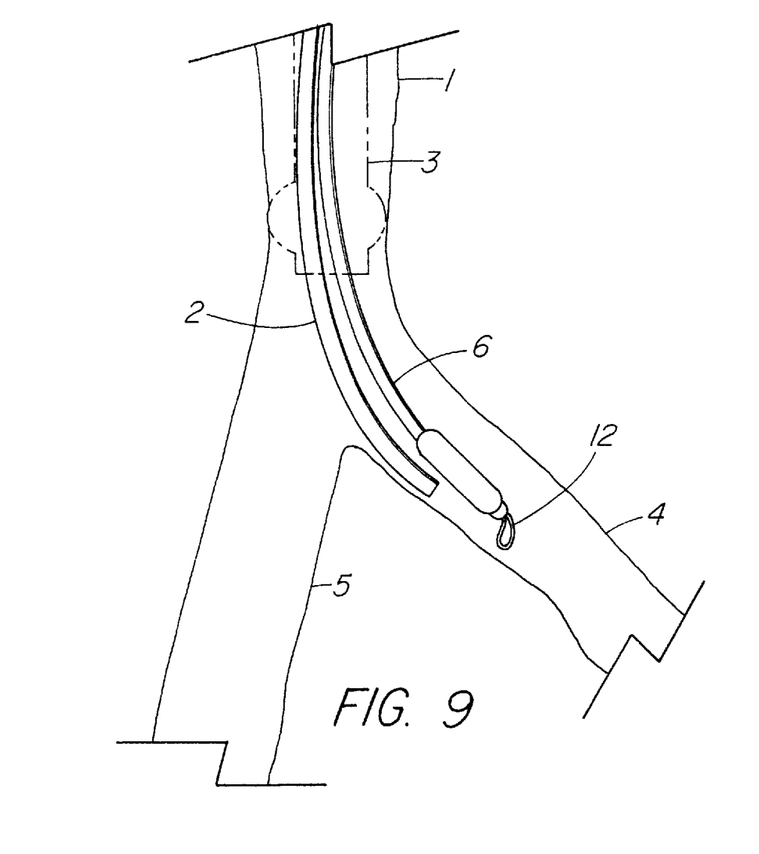
FIG. 9 depicts a profile view of the trachea with the endobronchial blocker catheter advanced off the fiberoptic bronchoscope into the left mainstem bronchus.

In FIG. 9, the endobronchial blocker catheter 6 with wire guide loop 12, has been advanced over the fiberoptic bronchoscope 2, and the unencased wire guide loop 12 has exited off the distal end of the fiberoptic bronchoscope into the left mainstem bronchus 4. The fiberoptic bronchoscope 2 has acted as a guide or stint for the endobronchial blocker catheter with the wire guide loop 12 extending distally therefrom. The unencased wire guide loop rides along the fiberoptic bronchoscope, thereby allowing the endobronchial blocker catheter to navigate sharp bends in the trachea such as the left mainstem bronchus 4 or any other sharp bends in the tracheo-bronchial tree. Without wire guide 14 or loop 12, entry of an endobronchial blocker catheter into an area of the trachea with sharp bends such as the left mainstem bronchus 4 is problematic, difficult, time consuming, and damaging to the trachea because of the multiple attempts it takes and the repeated hitting of the tracheal wall by an endobronchial blocker catheter to gain entrance into the desired airway passage.

Figure 10:
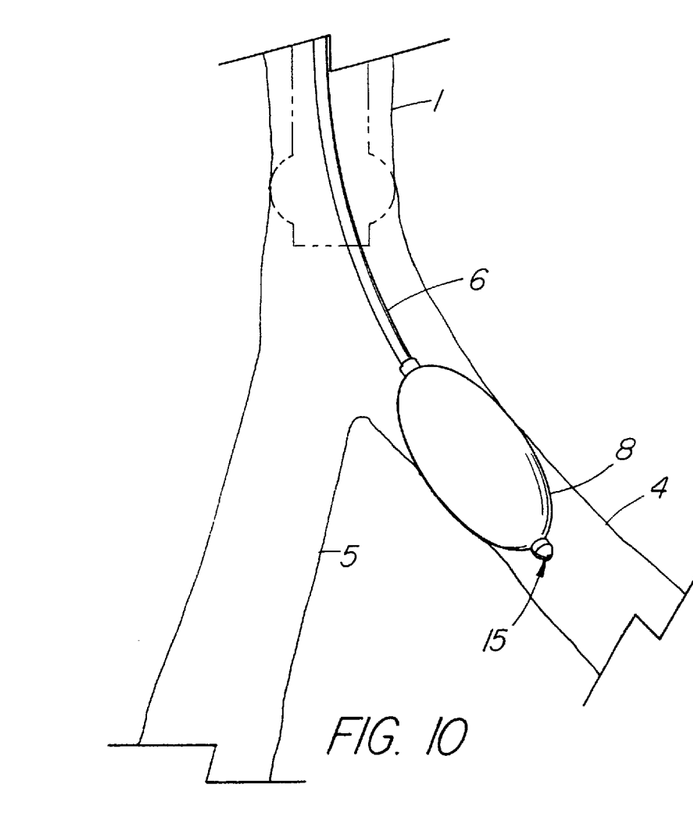
FIG. 10 depicts a profile view of the trachea with the endobronchial blocker catheter in left mainstem bronchus, the wire guide removed and balloon inflated.

FIG. 10 depicts endobronchial blocker catheter 6 with wire guide 14 removed and blocker balloon 8 inflated. The endobronchial blocker catheter is in the left mainstem bronchus 4 and will prevent ventilation from reaching lung areas distal to the inflated balloon. With the wire guide removed, the large endobronchial blocker lumen 15 allows communication from the sealed lung segment to the proximal threaded port. Either fluid or gas can then be added or removed from the sealed lung segment.

Thus, it can be appreciated that the fiberoptically directable wire guided multiple lumen endobronchial blocker catheter provides a means of placing an endobronchial blocker catheter using a fiberoptic bronchoscope to navigate sharp bends in the tracheo-bronchial tree, which are normally very difficult or impossible to enter with an endobronchial blocker or any type of catheter. The fiberoptically directable wire guided multiple lumen endobronchial blocker catheter allows the average clinician to place an endobronchial blocker catheter or any catheter using average clinical skills in a timely, nonproblematic fashion with minimal trauma to the airway. Furthermore, the fiberoptically directable endobronchial blocker catheter has the following advantages in that:

1) It incorporates a balloon inflation system in which the inflated balloon is elliptical in shape to increase surface area contact; is of a low pressure, high compliance, high volume type to minimize damage to the airway lining; and incorporates a pneumatic bladder with a self sealing spring valve for inflation to provide a tactile sense of the balloon inflation pressure.

2) It incorporates a catheter design with stainless steel mandrel wires which do not extend to the catheter tip providing stiffness to the main body of the catheter while allowing the tip to be less stiff to minimize the chance of tissue damage while said catheter is advanced.

3) It incorporates a plastic tube made of a radiopaque material to allow placement to be ascertained by fluoroscopy or roentgenogram.

4) It incorporates a wire guide clamp device using either a locking cam or screw tensioner.

5) It incorporates first and second catheter lumens: a small lumen for balloon inflation; and a second, larger lumen, which encases a long wire guide loop exiting as a smaller loop at the catheter end or acting as a lumen for the addition or removal of either gas or liquid from the blocked lung segment after the long wire guide loop is removed.

While the above description contains many specifics, it should not be construed as limitation of the scope of the invention, but rather as an example of a preferred embodiment thereof. Many other variations are possible. The wire guide loop exiting as small unencased loop at the catheter distal end, or any small unencased loop at the distal catheter end, which is coupled to the motion of a fiberoptic bronchoscope placed in the tracheo-bronchial tree placed through the small unencased loop can be used to place any type of catheter into the tracheo-bronchial tree. The fiberoptic bronchoscope acts as a guide for the catheter and is able to navigate sharp bends in the tracheo-bronchial tree, which an endobronchial blocker or any catheter would not enter without difficulty. The small unencased loop allows the endobronchial blocker or any catheter to ride the bronchoscope to the correct position. It is also contemplated that the loop or guidance means be simply affixed to the distal end of the elongated member to position the endoscope therethrough. The larger lumen of the previously described elongated member is not absolutely required and can be included or deleted as optionally desired.

What is claimed is:

1. A guided endobronchial blocker catheter (6) comprising an elongated member (7) with first and second lumens (15, 16) therein and with an inflatable blocker balloon (8) disposed about a distal portion (35) of the elongated member, one (16) of the lumens extending to an interior (7) of the balloon in order to accomplish inflation, and a wire (14) including a loop (12) which extends from a distal end of an other (15) of the lumens, whereby a fiberoptic endoscope (2) can be positioned through the loop to a desired site for the blocker balloon, and the catheter can then be guided by the endoscope to the desired inflation site via the loop.

2. The catheter according to claim 1, wherein the blocker balloon is an elliptical shaped balloon and wherein the endoscope is a fiberoptic bronchoscope incorporating a tip control mechanism to permit visualization and navigation.

3. The catheter according to claim 1, wherein the loop extends from a distal end (36) of the elongated member, and at least one proximal end (37) of the loop is fixed relative to a proximal end (38) of the catheter.

4. The catheter according to claim 3, wherein the at least one proximal end is rotatable relative to the elongated member to permit rotation of the loop in order to provide alignment with the endoscope.

5. The catheter according to claim 3, wherein an other end (33) of the loop extends past the proximal end of the catheter and can be pulled to decrease a size of the loop and pushed to increase it.

6. The catheter according to claim 5, wherein a clamp (39; 23–25; 27, 29, 30) is provided at the proximal end of the catheter for clamping the other end of the loop in a fixed position.

7. The catheter according to claim 3, wherein the proximal end of the catheter is provided with a threaded port (20) and both proximal ends (37) of the loop are fixed to a threaded end cap (21) adjustably engageable on the threaded port.

8. The catheter according to claim 5, wherein the other end (33) of the loop passes through a hole (31) in the end cap, and is engaged by a cam support fixture (23) disposed about the proximal end of the catheter.

9. The catheter according to claim 5, wherein the other end (33) of the loop passes through a hole (31) in the end cap, and is engaged and fixed by a screw (39).

10. A guided endobronchial blocker catheter (6) comprising an elongated member (13) with a blocker balloon (8) disposed about a distal end (36) of the elongated member and a lumen (16) in the elongated member for inflating the balloon, wherein the distal end of the elongated member is provided with guidance means (12, 14) for engagement with an endoscope for guiding the catheter in an anatomical passage.

11. The catheter according to claim 10, wherein said guidance means includes a loop (12) extending from a distal end (36) of the elongated member.

12. The catheter according to claim 11, wherein said elongated member includes an other lumen (15) extending therein for receiving a wire (14) of said guidance means therein.

13. The catheter according to claim 1, wherein the blocker balloon is an elliptical shaped balloon and wherein the endoscope is a fiberoptic bronchoscope incorporating a tip control mechanism to permit visualization and navigation.

14. The catheter according to claim 1, wherein the loop extends from a distal end (36) of the elongated member, and at least one proximal end (37) of the loop is fixed relative to a proximal end (38) of the catheter.

15. The catheter according to claim 14, wherein the at least one proximal end is rotatable relative to the elongated member to permit rotation of the loop in order to provide alignment with the endoscope.

16. The catheter according to claim 14, wherein an other end (33) of the loop extends past the proximal end of the catheter and can be pulled to decrease a size of the loop and pushed to increase it.

17. The catheter according to claim 16, wherein a clamp (39; 23–25; 27, 29, 30) is provided at the proximal end of the catheter for clamping the other end of the loop in a fixed position.

18. The catheter according to claim 14, wherein the proximal end of the catheter is provided with a threaded port (20) and both proximal ends (37) of the loop are fixed to a threaded end cap (21) adjustably engageable on the threaded port.

19. The catheter according to claim 16, wherein the other end (33) of the loop passes through a hole (31) in the end cap, and is engaged by a cam support fixture (23) disposed about the proximal end of the catheter.

20. A method of catheterizing tubular convoluted anatomical passageways using a flexible fiberoptic endoscope (2) and a flexible loop tipped catheter (6), comprising the steps of:

inserting the flexible fiberoptic endoscope through a distal loop (12) of said catheter;

inserting the flexible fiberoptic endoscope under direct continuous visualization into said anatomic passageway;

using said fiberoptics of said scope to locate and identify the position to catheterize;

advancing the catheter along the longitudinal axis of the fiberoptic endoscope using the circumferentially placed loop; and positioning visually the catheter by advancing the loop off the distal end of said fiberoptic bronchoscope and retracting or advancing said catheter into optimal positioning under direct vision.

* * * * *